(12) United States Patent
Kuri-Harcuch et al.

(10) Patent No.: US 6,541,028 B1
(45) Date of Patent: Apr. 1, 2003

(54) METHODS FOR PROMOTING HEALING OF CORNEAL RESURFACING WOUNDS

(75) Inventors: Walid Kuri-Harcuch, Brookline, MA (US); Federico Castro Munozledo, Chapultepec (MX)

(73) Assignee: Celadon Science, LLC, Wellesley, MA (US)

(*) Notice: Subject to any disclaimer, the term of this patent is extended or adjusted under 35 U.S.C. 154(b) by 0 days.

(21) Appl. No.: 09/341,733

(22) PCT Filed: Jan. 16, 1998

(86) PCT No.: PCT/US98/00820
§ 371 (c)(1),
(2), (4) Date: Oct. 19, 1999

(87) PCT Pub. No.: WO98/31316
PCT Pub. Date: Jul. 23, 1998

Related U.S. Application Data
(60) Provisional application No. 60/037,747, filed on Jan. 17, 1997.

(51) Int. Cl.⁷ .............. A61F 13/00; A61K 9/70; A61L 15/16
(52) U.S. Cl. ............ 424/443; 424/444; 424/445; 424/427
(58) Field of Search ............... 424/443, 445, 424/444, 427

(56) References Cited

U.S. PATENT DOCUMENTS

| | | |
|---|---|---|
| 4,865,871 A | 9/1989 | Livesey et al. |
| 5,145,770 A * | 9/1992 | Tubo et al. .......... 435/1 |
| 5,197,985 A | 3/1993 | Caplan et al. |
| 5,298,417 A | 3/1994 | Cancedda et al. |
| 5,401,510 A * | 3/1995 | Robertson et al. ......... 424/427 |
| 5,405,742 A | 4/1995 | Taylor |
| 5,440,018 A | 8/1995 | Ohmura et al. |
| 5,580,714 A | 12/1996 | Polovina |
| 5,580,781 A | 12/1996 | Naughton et al. |

FOREIGN PATENT DOCUMENTS

WO  WO 94/13135 A1  6/1994

OTHER PUBLICATIONS

Reiners et al., "Cryopreservation of Human Granulocyte–Macrophage Progenitor Cells (CFU–c) with Dimethyl Sulfoxide (DMSO) and Human Serum Albumin", Cryo–Letters, (1986), 7:327–337, pub. Cambridge, U.K.

Storey, "Biochemistry of natural freeze tolerance in animals: molecular adaptations and applications to cryopreservation", Biochemistry and Cell Biology, Apr., 1990, vol. 68–No. 4, pp–687–698, pub. Ottawa, Ont.

* cited by examiner

Primary Examiner—Thurman K. Page
Assistant Examiner—S. Howard
(74) Attorney, Agent, or Firm—Wolf, Greenfield & Sacks, P.C.

(57) ABSTRACT

The present invention provides methods for promoting healing of wounds which result from corneal resurfacing procedures, e.g. from laser surgery to alter refractive of the eye. The methods involve the application of a sheet of cultured epithelial cells to the laser corneal resurfacing wound of a subject in need of such treatment. The methods promote faster healing of corneal resurfacing wounds relative to prior art methods of healing such wounds. The invention also provides corneal wound healing devices having the shape and dimensions of a contact lens.

16 Claims, 1 Drawing Sheet

METHODS FOR PROMOTING HEALING OF CORNEAL RESURFACING WOUNDS

This application is a 371 of PCT/US98/00820 filed Jan. 16,1998.

FIELD OF THE INVENTION

The invention involves methods of using sheets of cultured epithelial cells to promote healing of corneal resurfacing wounds.

BACKGROUND OF THE INVENTION

Treatment of refraction defects such as spherical ametropias (myopia and hypermetropia) and cylindrical ametropias (astigmatism) has progressed in recent years beyond application of prosthetic devices designed to correct the defects, including eyeglasses and contact lenses. Surgical procedures are now commonly performed to achieve a measure of permanence in the correction of refraction defects. For example, radial keratotomy (RK) is a surgical procedure which corrects the shape of the eye by placing radial incisions in the periphery of the eye to change the curvature of the cornea. More recent advances include the treatment known as photorefractive keratectomy (PRK). In PRK, a laser is used to reshape the surface of the cornea by ablating a portion of the outer layers of the cornea. The preferred laser for PRK is the excimer laser which emits radiation with a wavelength of 193 nm. At this wavelength, photoablation results without thermal damage to deeper cells. PRK differs from RK and other surgical procedures by not altering the inner layers of the cornea (corneal endothelium); in PRK, only the outer layers of cells of the cornea are removed. On the other hand, in other laser procedures such as laser in situ keratomileusis (LASIK), ablation of stromal tissue is performed.

One of the difficulties which accompanies laser corneal resurfacing and LASIK procedures is the often painful post-treatment period. Most, if not all, patients suffer very intense pain during the first postoperative day. Many patients experience pain for several days after the completion of the PRK procedure.

Other postoperative symptoms of PRK and LASIK include photophobia, corneal opacity (haze) and corneal scarring. The typical recovery time for the regrowth of the corneal epithelium (reepithelialization) following PRK or LASIK is about 7 to 10 days. The degree of scarring has been reported to be a function of the time required for reepithelialization of the corneal surface (Wu et al., Arch. Ophthalmol. 109:1426–1432, 1991). Wu et al. also reported that residual stromal haze and scarring prevented significant improvement of vision in certain patients.

Present treatments for adverse effects associated with PRK rely on the administration of drugs. For example, Robertson et al. (U.S. Pat. No. 5,401,510) disclose the topical administration of non-steroidal antiinflammatory drugs such as ketorolac and diclofenac to the eye after PRK. While effective in the management of the intense pain associated with PRK, these non-steroidal drugs may slow epithelialization of the corneal laser wound. Robertson et al. also disclose the administration of wound healing modulators to the eye after PRK for the reduction of corneal haze. Such modulators are formulated as solutions, suspensions, emulsions, gels or delivered via use of a solid matrix such as a collagen shield or contact lens. The wound healing modulators are administered to enhance wound healing, prevent improper collagen repair, prevent improper epithelial cell coverage of the cornea and prevent inflammation. Robertson does not disclose the use of epithelial cells for promotion of wound healing.

The drawbacks of the prior art procedures include the side effects of topical anti-inflammatory drugs administered for pain management, the need to change corneal dressings, and the need to reapply healing and anti-pain agents to the cornea, all of which can exacerbate pain and expose the corneal resurfacing wound to biological and non-biological contaminants.

Thus, there is a need for a treatment of laser corneal resurfacing wound sites that will promote faster healing of the wound, lessen pain and reduce the possibility of lasting complications associated with the healing process, such as corneal scarring and haze. Additionally, there is a need for a treatment which need not be changed while the corneal resurfacing wound heals.

Sheets of cultivated human epithelial cells have been used as a replacement for skin and as a biological wound dressing. The culture of epithelial cells was pioneered in 1975 by Dr. Howard Green, which discovery served as the basis for both autograft and allograft wound healing technology. The first therapeutic product made from cultivated human epithelial cells was an autograft, where a patient's cells were cultured and returned to the same patient. The cells establish themselves at the wound site permanently. This technology has been used successfully to treat skin burns and other epidermal lesions such as ulcers.

The allograft technology involves treating a patient with cultured cells from tissue of a diferent individual. Such cells do not establish themselves permanently, but instead can be applied as a biological dressing for wounds, including partial thickness burns and healing of split-thickness autograft donor sites (see, e.g., EP 0 296 475, Cancedda et al.; PCT/US91/03582, Tubo et al.) Commercial allografts are not known to the inventors.

SUMMARY OF THE INVENTION

The present invention provides methods for promoting healing of corneal wounds, especially those wounds which result from laser surgery to alter refraction by the eye. The methods promote faster healing of corneal resurfacing wounds relative to prior art methods of healing such wounds. The methods are believed to reduce pain associated with corneal resurfacing wounds. The methods also are believed to reduce complications associated with the healing process, such as corneal scarring and haze. The methods involve the application of sheets of cultured epithelial cells to the cornea of a subject in need of such treatment.

According to one aspect of the invention, a method for promoting healing of a corneal wound is provided. The method involves applying a sheet of cultured epithelial cells to the wound of a patient in need of such treatment. Preferably, the sheet substantially covers the wound. The corneal wound, in preferred embodiments, is a laser resurfacing wound.

In certain embodiments, the sheet of cultured epithelial cells is a preserved sheet. The preserved sheet of cultured epithelial cells can be dried. If the preserved sheet of cells exists in a dry state, then it can be applied to the wound after rehydration or applied directly to the wound without prior rehydration, the dried cells rehydrating at the wound site.

In other embodiments, the sheet of cultured epithelial cells is disposed on a substratum. The cells can be attached to a substratum such as hyaluronic acid, collagen, fibrin glue, synthetic products and the like. The substratum can provide structural support to the sheet of cells during the step of applying the sheet to the wound.

In yet other embodiments, the sheet of cultured epithelial cells is disposed on a backing. The backing can provide, inler alia, structural support to the sheet of cells during the step of applying the sheet to the wound. Preferably, the backing is a contact lens or is a substrate configured like a contact lens. The method optionally provides for covering the applied sheet of cultured epithelial cells with a dressing.

In still other embodiments, the cultured epithelial cells are attached to a substratum or mixed with a gel. Preferably, the substratum is selected from the group consisting of microbeads, hyaluronic acid, collagen, fibrin glue and polymers.

In certain embodiments, the laser corneal resurfacing wound results from a laser eye surgical procedure selected from the group consisting of PRK and LASIK.

According to another aspect of the invention, a corneal wound healing device is provided. The device includes a substrate having an arcuate shape which conforms to the shape of an eye, such as the shape and dimensions of a contact lens, defining an inner concave surface. Cultured epithelial cells are attached to the inner concave surface of the substrate. In preferred embodiments the cultured epithelial cells are attached as a sheet. This device then may be applied to an eye according, for example, to the methods described above.

The invention also involves the use of cultured epithelial cells, preferably in the form of a sheet, in the preparation of a medicament for treating a corneal wound. The corneal wound in one aspect of the invention is created by laser treatment, preferably laser resurfacing treatment. The epithelial cells provide cell-cell contact, growth and/or healing factors and a covering, thereby acting as a biological wound dressing.

DETAILED DESCRIPTION OF THE INVENTION

Figure 1:
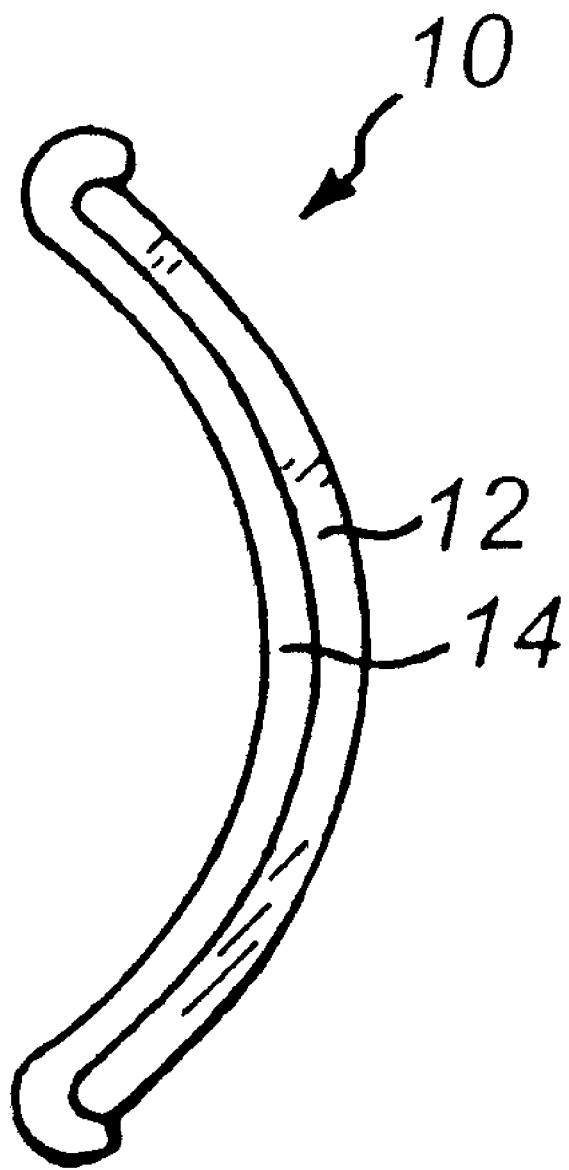
FIG. 1 is a partial cross-sectional view of a corneal wound healing device of the invention.

The invention involves novel methods of promoting healing of a laser corneal resurfacing wound. The methods involve the application to the laser corneal resurfacing wound of a prepared sheet of cultured epithelial cells. Preparation of such a sheet of cultured epithelial cells is disclosed, for example, in PCT Patent Application PCT/US95/14648. By "applying" is meant placing the sheet of cultured epithelial cells over the wound and, optionally, covering the sheet of cultured epithelial cells with a dressing. Thus, applying a sheet of cultured epithelial cells is performed according to any standard medical procedure for applying a dressing to a corneal wound. If necessary, after applying it, one can attach the sheet of cultured epithelial cells to the tissue surrounding the laser corneal resurfacing wound by means of an ophthalmologically-acceptable adhesive, for instance a biological adhesive such as fibrin glue.

The laser corneal resurfacing wound is created during the process of corneal resurfacing. Corneas can be "resurfaced" by the use of a laser, such as an excimer laser. Other lasers useful for performing corneal resurfacing will be known to one of ordinary skill in the art. By "resurfacing" is meant the removal of selected portions of tissue, particularly the upper (i.e. outer) layer of the cornea, to achieve a desired correction of refraction. The laser emits a beam of light which imparts energy to the outer layer of the cornea in a highly localized fashion. The outer layer of the cornea (or the outer layer of the corneal stroma in the LASIK procedure) contacted by the laser beam is vaporized, thus correcting the curvature of the cornea to restore proper light refraction by the cornea. The laser does not damage the deeper (i.e. inner) layers of the cornea. In order to cover the wound, keratinocytes originating in the limbus located at the perimeter of the corneal epithelium must migrate centrally and by proliferating and differentiating reconstitute a stratified corneal epithelium.

Prior art therapies for promoting healing of a laser corneal resurfacing wound include the application of ointments and/or a drug, which must be reapplied as the concentration of the drug falls below an effective amount of the drug.

The application of a sheet of cultured epithelial cells enhances the healing process by providing to the wound growth factors, extracellular matrix components and other wound healing agents. The present invention facilitates the application of a physiologically relevant amount of growth factors, extracellular matrix components and other wound healing agents at the wound site. Additional applications of wound healing agents are not required.

The method of the invention also facilitates application of a physiologically relevant spectrum of wound healing agents. The sheet of cultured epithelial cells, once applied, releases factors which promote the proliferation and/or differentiation of uninjured corneal epithelial cells which migrate to heal the wound. For example, a sheet of cultured epithelial cells can secrete known growth factors such as transforming growth factor alpha (TGFα), fibroblast growth factors (FGFs), basement membrane constituents and the like, but also will secrete growth factors and other wound healing agents which have not been characterized.

Of course, like prior art methods which apply a traditional wound dressing to the laser corneal resurfacing wound, the methods of applying a cultured epithelial cell sheet provide a protective barrier to the laser wound which excludes foreign matter including microorganisms such as bacteria and viruses.

Laser corneal resurfacing procedures may remove tissue to various depths, depending on the amount of correction of corneal curvature required to improve refraction. The methods disclosed herein are effective for promoting healing of laser corneal resurfacing wounds of the outer corneal cell layers because the sheet of cultured epithelial cells releases wound healing agents which, inter alia, promote corneal epithelial cells inmigrating inwardly from the limbus. Thus, treatment of laser corneal resurfacing wounds of the outer corneal cell layers is enhanced using the present methods.

A subject is treatable according to the methods disclosed herein regardless of the subject's genotype because the healing process promoted by the application of a sheet of cultured epithelial cells is not specific to the genetic makeup of the subject. Thus, the cells which constitute the sheet of cultured epithelial cells can be derived from multiple sources, e.g. from a single or from a mixed population of donors. Thus, the method accommodates application of non-syngencic or non-autologous cells. In other words, the sheet of cells is not an autograft. The sheet of cultured epithelial cells is not required to be autologous because the cells of the sheet will not form the healed corneal epithelium, but instead will promote the healing by the recipient's own corneal epithelial cells. In treatment after LASIK procedures, the epithelial sheet promotes a faster reorganization and regeneration of stromal tissue.

The method also contemplates the use of xenogeneic cells (i.e. from other species) in the sheet of cultured epithelial cells. Allogeneic and xenogeneic cells optionally may be genetically manipulated to secrete a desired spectrum of wound healing agents such as human growth factors, cytokines and the like.

The sheet of cultured epithelial cells can be composed of virtually any epithelial cells, and preferably is composed of those capable of forming a sheet (see, e.g., PCT Patent Application PCT/US95/14648). The sheets may be composed of multiple types of cells, e.g. keratinocytes and fibroblasts, or may be composed of a single type of cells. Preferably, the sheet of cultured epithelial cells consists essentially of epidermal keratinocytes and/or corneal keratinocytes. Green and collaborators described a method for culturing human epiderrnal keratinocytes (Rheinwald & Green, Cell 6:331–343, 1975), that has been extended to other cultured epithelial cells. Under such culture conditions, stratified epithelial sheets suitable for transplantation onto large burn surfaces, ulcerations and other skin wounds are obtained (Gallico et al., *New Eng. J. Med.* 311:448–451, 1984; Heighten et al., *J. Am. Acad. Dermatol.* 14:399–405, 1986). The cultured epithelia obtained through this procedure have also been used as allografts for temporary wound dressing of burns (T. J. Phillips et al., *J. Am. Acad Dermatol.* 21:191, 1989; Bolivar-Flores et al., *Burns* 16:3–8, 1990). Cultured epithelial sheets prepared as described in the above-referenced articles are useful in the methods of the present invention.

In certain embodiments of the invention, the sheet of cultured epithelial cells applied to the laser corneal resurfacing wound is a preserved sheet of cultured epithelial cells. Preserved sheets of cultured epithelial cells and preferred methods for their preparation are disclosed in PCT Patent Application PCT/US95/14648. Other methods for preservation of cultured epithelial cell sheets are based on the use of glycerol or dimethyl sulfoxide as cryoprotectants, following a specific freezing protocol (see Cancedda and De Luca, 1994, U.S. Pat. No. 5,298,417). Still other preservation methods are based on cryopreservation using media containing both cell-penetrating glass-forming agents (specifically glycerol) and non-penetrating protectant agents (preferably polyvinylpyrrolidone (PVP), dextran or liydroxyethyl starch) (see Tubo et al, 1992, U.S. Pat. No. 5,145, 770).

In one important embodiment, the sheet of cultured epithelial cells is preserved in a dried state, for example as described in PCT patent application PCT/US95/14648. In such a case, the preserved sheet can be directly applied to the wound without rehydration, or can be rehydrated and subsequently applied to the wound site. Rehydration can be achieved by placing the sheet in a solution having physiologically-acceptable parameters (such as pH and osmolarity) for a time sufficient to rehydrate the cultured epithelial cells. Of course, the rehydration process must maintain the structural and functional characteristics of the cultured epithelial sheet. Rehydration solutions include phosphate-buffered saline, Tris-buffered saline, Ringer's solution, and the like.

In other embodiments, the sheet of cultured epithelial cells can be preserved in a frozen state, as described in PCT Patent Application PCT/US95/14648. When a frozen cultured epithelial cell sheet is used according to the invention, the sheet is thawed prior to applying it to the laser corneal resurfacing wound. Methods for thawing the culture epithelial cell sheet which do not compromise the structural or functional integrity of the sheet can be used and will be known to one of ordinary skill in the art.

Optionally, the sheet of cultured epithelial cells can be applied to the laser corneal resurfacing wound on a backing to facilitate manipulation of the sheet. Suitable backings include gauze, plastics, silicones, and hydrogels. Preferably the backing is in the form of a contact lens, which facilitates the application of the sheet of cultured epithelial cells. When applied with a backing, the backing optionally can be removed after positioning the cell sheet at the wound site, and the cell sheet covered with a dressing. Alternatively, the backing can be left attached to the cell sheet to serve as an outer protectant layer. The cells may also be attached to (e.g., grown on) a substratum as disclosed in U.S. patent application Ser. No. 08/337,162, such as microbeads, hyaluronic acid, collagen, fibrin glue, synthetic products and the like. Preferably, synthetic products useful in the invention include polymers, particularly ophthalmically-acceptable polymers as will be be known to the skilled artisan. In such cases, the substratum can be attached to a backing if desired. The cultured epithelial cells can also be mixed with a gel, and then applied to the laser resurfacing wound. Preferably, the gel is an ophthalmically-acceptable gel.

The laser corneal resurfacing wound typically is the result of a laser eye surgical procedure. For example, the wound can result from photorefractive keratectomy (PRK), wherein a laser is used to reshape the surface of the cornea by ablating a portion of the outer layers of the cornea. The wound can also result from, e.g., laser in situ keratomileusis (LASIK), ablation of stromal tissue is performed. Other laser procedures which produce corneal wounds. will be known to the skilled artisan.

The invention provides in another aspect a method for healing a corneal wound. The corneal wound can be the result of a corneal disease state such as a trophic ulcer.

According to another aspect of the invention, a corneal wound healing device is provided.

The device includes cultured epithelial cells and a substrate which acts as a backing for the cultured epithelial cells. The substrate is configured to fit upon the curved surface of the eye, for example, like a contact lens. Thus, it can have the shape and dimensions of a contact lens. The shape and dimensions can be varied according to the needs of the user based on the shape and size of the eye and the shape and size of the corneal wound. The substrate can be any opthalmically acceptable contact lens material, which materials are well known in the art.

The substrate, when configured like a contact lens, has an inner concave surface and an outer convex surface. Epithelial cells can be attached to the inner concave surface of the substrate by a variety of means known to those of skill in the art. In short, the sheet of cells is applied to the inner concave surface of the lens and the free ends are folded over the edges and onto the outer convex surface of[] the lens. Preferably, the cultured epithelial cells described herein are attached as a sheet of cells.

Referring to FIG. 1, a corneal wound healing device 10 is depicted. The device 10 is a contact lens 12 having layered on its inner, concave surface a sheet 14 of cultured epithelial cells. The sheet can be held in place with a glue, if desired, such as fibrin glue, synthetic polymers and the like.

EXAMPLE

This example describes the treatment of a subject having laser corneal resurfacing wounds with the disclosed epithelial cell sheets and with the traditional method of healing such wounds. The subject is subjected to excimer laser treatment of both corneas for treatment of myopia.

Epithelial cell sheets are prepared as described in PCT Patent Application PCT/US95/14648. Briefly, epidermal sheets were obtained by culturing human neonatal foreskin keratinocytes, using the procedures developed by Rheinwald & Green (1975). The epithelial sheets were detached from culture dishes using Dispase II (Boehringer Mannheim) at a final concentration of 2.5 mg/ml. After detaching from culture dishes, the epithelial sheets are washed with phosphate buffered saline (PBS) at room temperature, optionally are mounted in or on a backing material, and are used as needed. If the epithelial cell sheets are to be preserved for late use, then following the PBS wash the sheets are incubated for 10 minutes with preservation solution consisting in Dulbecco-Vögt modification of Minimal Esential Medium (DMEM) containing glucose and human serum albumin; if desired, preservation solution may be buffered with 20.0 mM HEPES. After incubation, the preservation solution is aspirated leaving the minimum volume of solution in the vessel containing the epithelium. Afterwards, epithelia, which may be mounted on a backing material including for example, vaseline coated gauze or a contact lens, are placed in heat-sealed bags and frozen. The epithelial sheets also can be dried.

An epithelial sheet, attached to a device configured like a contact lens, is removed from the container in which it is stored, and applied aseptically to the laser resurfacing wound present on the right cornea of the subject. The left cornea of the subject is treated according to standard laser resurfacing wound healing practices. The subject observes reduced pain and discomfort during the healing process at the site of the right cornea laser resurfacing wound, which is treated with the epithelial cell sheet, relative to left cornea laser resurfacing wound, which is treated with the art standard treatments. The epithelial cell sheet is removed before the standard treatment can be discontinued, indicating that the epithelial cell sheet shortens the time required for complete healing of the laser corneal resurfacing wounds. The sheet is removed after reepithelialization, which typically takes 1–2 days.

All patents and other documents disclosed in this application are incorporated in their entirety herein by reference.

While the invention has been described with respect to certain embodiments, it should be appreciated that many modifications and changes may be made by those of ordinary skill in the art without departing from the spirit of the invention. It is intended that such modification, changes and equivalents fall within the scope of the following claims.

What is claimed is:

1. A method for promoting healing of a laser corneal resurfacing wound comprising applying to the laser corneal resurfacing wound of a subject in need of such treatment a sheet of cultured epithelial cells, wherein the cells are allogeneic or xenogeneic to the subject.

2. The method of claim 1, wherein the sheet of cultured epithelial cells substantially covers the wound.

3. The method of claim 2, wherein the sheet of cultured epithelial cells consists essentially of epidermal keratinocytes or corneal keratinocytes.

4. The method of claim 1, wherein the sheet of cultured epithelial cells is a preserved sheet of cultured epithelial cells.

5. The method of claim 4, wherein the preserved sheet of cultured epithelial cells is dried.

6. The method of claim 1 wherein the sheet of cultured epithelial cells is applied to the wound on a substratum.

7. The method of claim 1 wherein the sheet of cultured epithelial cells is applied to the wound on a backing.

8. The method of claim 7, wherein the backing is in the shape of a contact lens.

9. The method of claim 1, further comprising covering the sheet of cultured epithelial cells, after application to the wound, with a dressing.

10. The method of claim 1, wherein the cultured epithelial cells are attached to a substratum or mixed with a gel.

11. The method of claim 10, wherein the substratum is selected from the group consisting of microbeads, hyaluronic acid, collagen, fibrin glue and polymers.

12. The method of claim 1, wherein the laser corneal resurfacing wound results from a laser eye surgical procedure selected from the group consisting of PRK and LASIK.

13. A method for promoting healing of a corneal wound comprising applying to the corneal wound of a subject in need of such treatment a sheet of cultured epithelial cells.

14. The method of claim 13, wherein the corneal wound is a trophic ulcer.

15. A corneal wound healing device comprising a substrate having the shape and dimensions of a contact lens, and defining an inner concave surface and cultured epithelial cells attached to the inner concave surface.

16. The corneal wound healing device of claim 15, wherein the cultured epithelial cells are attached as a sheet.

* * * * *